United States Patent
Izumi et al.

(10) Patent No.: US 9,481,860 B2
(45) Date of Patent: Nov. 1, 2016

(54) METHOD FOR REMOVING BACTERIAL CONTAMINANTS FROM SACCHARIFIED SOLUTION AND FERMENTATION SYSTEM

(71) Applicant: KAWASAKI JUKOGYO KABUSHIKI KAISHA, Kobe-shi, Hyogo (JP)

(72) Inventors: Noriaki Izumi, Kobe (JP); Manabu Masamoto, Kobe (JP); Satoshi Konishi, Akashi (JP)

(73) Assignee: KAWASAKI JUKOGYO KABUSHIKI KAISHA, Kobe-shi (JP)

( * ) Notice: Subject to any disclaimer, the term of this patent is extended or adjusted under 35 U.S.C. 154(b) by 0 days.

(21) Appl. No.: 14/655,430

(22) PCT Filed: Dec. 3, 2013

(86) PCT No.: PCT/JP2013/007085
§ 371 (c)(1),
(2) Date: Jun. 25, 2015

(87) PCT Pub. No.: WO2014/103183
PCT Pub. Date: Jul. 3, 2014

(65) Prior Publication Data
US 2015/0337253 A1    Nov. 26, 2015

(30) Foreign Application Priority Data

Dec. 25, 2012    (JP) .................................. 2012-280900

(51) Int. Cl.
*C12M 1/26* (2006.01)
*B01D 61/14* (2006.01)
(Continued)

(52) U.S. Cl.
CPC ............. *C12M 33/14* (2013.01); *C12M 21/12* (2013.01); *C12M 29/18* (2013.01); *C12M 47/02* (2013.01);
(Continued)

(58) Field of Classification Search
CPC .. B01D 61/147; B01D 21/262; C12M 1/264; C12M 33/10
See application file for complete search history.

(56) References Cited

U.S. PATENT DOCUMENTS

| 4,460,687 A | * | 7/1984 | Ehnstrom | ................ C12P 7/06 435/161 |
| 4,952,503 A | | 8/1990 | Granstedt | |

(Continued)

FOREIGN PATENT DOCUMENTS

| CN | 85 1 09546 A | 8/1986 |
| CN | 101392273 A | 3/2009 |

(Continued)

OTHER PUBLICATIONS

Waites, Michael J., et al., "Industrial Microbiology: An Introduction", Blackwell Science, Inc., 2001, pp. 112-114.*

(Continued)

*Primary Examiner* — Krishnan S Menon
*Assistant Examiner* — Ryan B Huang
(74) *Attorney, Agent, or Firm* — Oliff PLC

(57) ABSTRACT

A method for removing bacterial contaminants from a saccharified solution capable of suppressing proliferation of bacterial contaminants in a fermentation tank without using an antibiotic in alcoholic fermentation of a biomass saccharified solution using normal yeast, and a fermentation system suited for conducting the method are provided. The method and system include drawing out a saccharified solution from a fermentation tank, conducting rough separation for recovering yeast from the solution, and conducting fine separation for removing bacterial contaminants from the solution, thereby removing only the contaminants while recovering yeast. The rough separation is through a filtering membrane having a pore size of 0.5 μm or more and 5 μm or less or centrifugal separation at 50G or higher and 500G or lower. The fine separation is through a filtering membrane having a pore size of 0.22 μm or less, or centrifugal separation at 1000G or higher and 15000G or lower.

1 Claim, 2 Drawing Sheets

(51) Int. Cl.
 *B01D 21/26* (2006.01)
 *C12M 1/00* (2006.01)
 *C12N 1/02* (2006.01)
 *C12N 1/16* (2006.01)
 *C12P 7/06* (2006.01)

(52) U.S. Cl.
 CPC ............ *C12M 47/12* (2013.01); *B01D 21/262* (2013.01); *B01D 61/147* (2013.01); *B01D 2311/2688* (2013.01); *C12N 1/02* (2013.01); *C12N 1/16* (2013.01); *C12P 7/06* (2013.01)

(56) References Cited

U.S. PATENT DOCUMENTS

2009/0061490 A1* 3/2009 Edwards .................. C12P 1/02
435/105

2011/0210001 A1 9/2011 Xu et al.

FOREIGN PATENT DOCUMENTS

| CN | 203741334 U | 7/2014 |
| JP | 2009-142219 A | 7/2009 |
| JP | 2011-092041 A | 5/2011 |

OTHER PUBLICATIONS

Mar. 1, 2016 Office Action issued in Chinese Application No. 201310715571.9.
Mar. 11, 2014 International Search Report issued in International Application No. PCT/JP2013/007085.
Jul. 1, 2015 Office Action issued in Chinese Patent Application No. 201310715571.9.

* cited by examiner

METHOD FOR REMOVING BACTERIAL CONTAMINANTS FROM SACCHARIFIED SOLUTION AND FERMENTATION SYSTEM

TECHNICAL FIELD

The present invention relates to a method for removing bacterial contaminants for preventing proliferation of bacterial contaminants in a saccharified solution in a fermentation tank in which hemicellulose or cellulose in lignocellulosic biomass such as wood biomass or herbal biomass is decomposed to saccharides by a known hydrolytic method such as a sulfuric acid, subcritical water method or enzymatic method, followed by ethanol fermentation with yeast. The present invention also relates to a fermentation system suited for conducting such a method for removing bacterial contaminants from a saccharified solution.

BACKGROUND ART

Lignocellulosic biomass including wooden biomass consists of about 20% of hemicellulose, about 50% of cellulose, and about 30% of lignin. Hemicellulose and cellulose are decomposed to saccharides by a saccharification treatment, and then the saccharides are fermented with a fermentation microorganism such as yeast, and thus ethanol can be produced. Saccharification of hemicellulose gives C5 saccharides and C6 saccharides, and saccharification of cellulose gives C6 saccharides.

The term C5 saccharides used herein refers to pentoses such as xylose or arabinose, and oligosaccharides thereof. The term C6 saccharides used herein refer to hexoses such as glucose or galactose, and oligosaccharides thereof.

In alcoholic fermentation of a biomass saccharified solution, yeast is principally used, and alcoholic fermentation is conducted in a fermentation tank for about 8 to 72 hours. However, since alcoholic fermentation occurs in a condition that bacterial contaminants (for example, *Leuconostoc*, *Citrobacter* or *Lactococcus* bacteria) are easy to proliferate, the saccharides will be consumed by bacterial contaminants when the saccharified solution is contaminated with the bacterial contaminants.

Further, bacterial contaminants include those inhibiting growth of yeast, and those inhibiting alcoholic fermentation with yeast. Therefore, if bacterial contaminants proliferate in the saccharified solution in the fermentation tank, ethanol yield decreases, and the economical practicability of bioethanol production can be impaired.

Patent Literature 1 discloses a continuous culture and fermentation device for ethanol-producing microorganism enabling perfectly continuous supply of a substrate and capable of continuous culture and fermentation of a specified ethanol-producing microorganism without leading deterioration in the productivity. In Patent Literature 1, a fermented solution (saccharified solution) is drawn out from the fermentation tank and solid-liquid separated, and the ethanol-producing microorganism is recovered into the fermentation tank. It is disclosed that penicillin, which is a β-lactam antibiotic, is preferably added to the fermented solution.

On the other hand, as an alcoholic fermentation method of a saccharified solution that does not involve an antibiotic, a method of suppressing proliferation of bacterial contaminants by adding acid also receives attention. Patent Literature 2 discloses yeast of *Candida glabrata* (NFRI3164 strain) capable of growing in the presence of 5% lactic acid as novel yeast having acid tolerance suited for alcoholic fermentation in the condition that proliferation of bacteria is suppressed by addition of acid.

CITATION LIST

Patent Literature

PTL 1: JP 2011-92041 A
PTL 2: JP 2009-142219 A

SUMMARY OF INVENTION

Technical Problem

As disclosed in Patent Literature 1, by adding an antibiotic to the fermentation tank of the biomass saccharified solution, it becomes possible to suppress proliferation of bacterial contaminants. However, since antibiotics are expensive, the production cost of bioethanol increases. If the antibiotic added to the saccharified solution (fermented solution) flows out into the external environment such as a sewage treatment facility, the activity of the activated sludge can be deteriorated, and thus it is necessary to provide a special facility for treating the antibiotic.

The specific yeast as disclosed in Patent Literature 2 is not inexpensive and not easily available unlike normal yeast for brewing. This is disadvantageous in producing bioethanol continuously and economically.

It is an object of the present invention to provide a method for removing bacterial contaminants from a saccharified solution capable of suppressing proliferation of bacterial contaminants in the fermentation tank without using an antibiotic or acid in alcoholic fermentation of a biomass saccharified solution using normal yeast, and a fermentation system suited for conducting the method for removing bacterial contaminants from a saccharified solution.

Solution to Problem

The inventors have made diligent efforts for solving the aforementioned problems, and found that it is possible to remove only bacterial contaminants from a saccharified solution while recovering yeast, by drawing out a saccharified solution (fermented solution) in a fermentation tank, conducting rough separation of recovering yeast from the saccharified solution, and then conducting fine separation of removing bacterial contaminants from the saccharified solution from which yeast has been separated, and have accomplished the present invention.

Concretely, the present invention relates to a method for removing bacterial contaminants from a saccharified solution, including, in a fermentation tank in which the saccharified solution is alcoholic fermented with yeast:

a rough separation step A of recovering yeast without recovering bacterial contaminants by drawing out part of the saccharified solution in the fermentation tank, and filtering the saccharified solution by means of a first membrane separator having a filtering membrane, or centrifugally separating the saccharified solution by a first centrifugal separator; and a fine separation step B of separating bacterial contaminants from the saccharified solution from which yeast has been recovered, by filtering the saccharified solution by a second membrane separator having a filtering membrane, or by centrifugally separating the saccharified solution by a second centrifugal separator after the rough separation step A;

wherein by returning the yeast recovered by the rough separation step A, and the saccharified solution from which bacterial contaminants have been separated by the fine separation step B to the fermentation tank, bacterial contaminants are selectively removed while yeast in the saccharified solution is recovered.

Preferably, the rough separation step A is a step A1 of filtering part of the saccharified solution by the first membrane separator having a filtering membrane having a pore size of 0.5 μm or more and 5 μm or less, or a step A2 of centrifugally separating part of the saccharified solution by the first centrifugal separator at 50G or higher and 500G or lower. Preferably, the fine separation step B is a step B1 of filtering the saccharified solution from which yeast has been recovered by the second membrane separator having a filtering membrane having a pore size of 0.22 μm or less, or a step B2 of centrifugally separating the saccharified solution from which yeast has been recovered by the second centrifugal separator at 1000G or higher and 15000G or lower.

It is impossible to sufficiently remove the bacterial contaminants only by filtering the saccharified solution. On the other hand, if the saccharified solution is subjected to membrane separation through a filtering membrane having a small pore size so as to sufficiently remove bacterial contaminants, the alcoholic fermentation efficiency decreases due to loss of yeast although bacterial contaminants are removed. In light of this, by first conducting the rough separation treatment A that recovers yeast which is larger than bacterial contaminants from the saccharified solution, and then conducting the fine separation treatment B that removes bacterial contaminant from the saccharified solution after the rough separation treatment, it becomes possible to remove only bacterial contaminants from the saccharified solution while recovering yeast. As a result, it becomes possible to suppress proliferation of bacterial contaminants in the fermentation tank.

As the rough separation treatment A, filtration by a membrane separator having a filtering membrane having pore size of 0.5 μm or more and 5 μm or less (step A1), or centrifugal separation by a centrifugal separator at 50G or higher and 500G or lower (step A2) can be selected. As the fine separation treatment B, filtration by a membrane separator having a filtering membrane having a pore size of 0.22 μm or less (step B1), or centrifugal separation by a centrifugal separator at 1000G or higher and 15000G or lower (step A2) can be selected.

By recovering yeast by the step A1 or the step A2, and removing bacterial contaminants from the saccharified solution by the step B1 or B2, and returning the saccharified solution from which yeast and bacterial contaminants have been removed, to the fermentation tank, it is possible to keep the fermentation efficiency high by preventing loss of yeast while suppressing proliferation of bacterial contaminants in the fermentation tank.

The present invention also relates to a fermentation system including:

a fermentation tank in which a saccharified solution is alcoholic fermented with yeast;

a rough separator for recovering yeast without recovering bacterial contaminants by drawing out part of the saccharified solution in the fermentation tank and filtering the saccharified solution by a first membrane separator having a filtering membrane, or by centrifugally separating the saccharified solution by a first centrifugal separator;

a fine separator for separating bacterial contaminants by filtering the saccharified solution from which yeast has been recovered from the rough separator by a second membrane separator having a filtering membrane, or by centrifugally separating the saccharified solution by a second centrifugal separator; and a path for returning the saccharified solution containing yeast obtained from the rough separator and the saccharified solution which is obtained from the fine separator and from which bacterial contaminants have been removed, to the fermentation tank, wherein the bacterial contaminants are selectively removed while yeast in the saccharified solution is recovered.

Preferably, the rough separator is the first membrane separator that conducts filtration through a filtering membrane having a pore size of 0.5 μm or more and 5 μm or less, or the first centrifugal separator that conducts centrifugal separation at 50G or higher and 500G or lower. Preferably, the fine separator is the second membrane separator that conducts filtration through a filtering membrane having a pore size of 0.22 μm or less, or the second centrifugal separator that conducts centrifugal separation at 1000 G or higher and 15000 G or lower.

Advantageous Effects of Invention

According to the present invention, it is possible to continuously suppress proliferation of bacterial contaminants in the fermentation tank of a biomass saccharified solution without necessity of adding an antibiotic or acid to the saccharified solution. Also special yeast is not required, and even when general brewing yeast is used, proliferation of bacterial contaminants in the fermentation tank can be suppressed.

DESCRIPTION OF EMBODIMENTS

Hereinafter, preferred embodiments of the present invention will be explained in reference to the drawings. The present invention is not limited to the following description.

Embodiment 1

Figure 1:
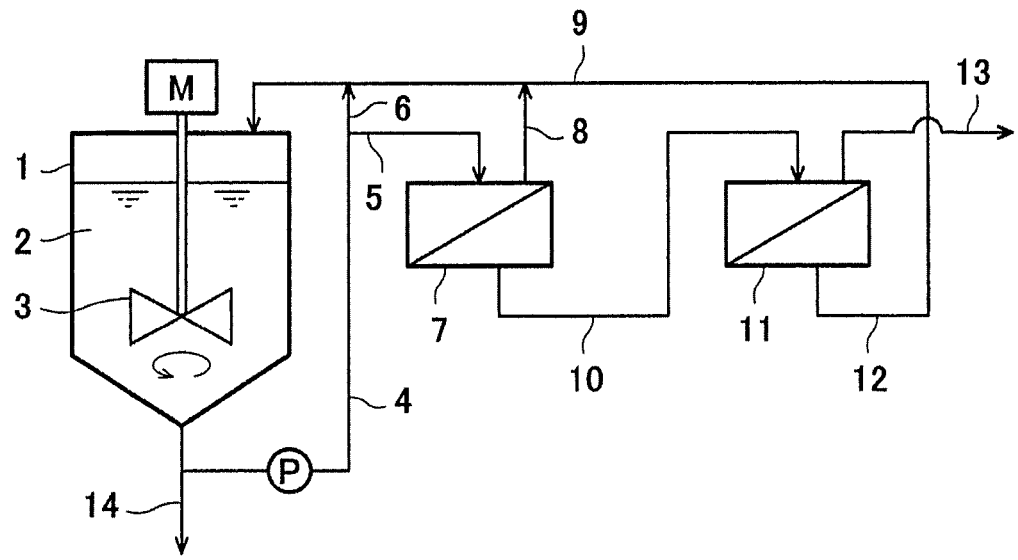
FIG. 1 is a schematic flowchart of a fermentation system according to Embodiment 1 of the present invention.

FIG. 1 is a schematic flowchart of a fermentation system according to Embodiment 1 of the present invention. A fermentation tank 1 stores a saccharified solution 2. The saccharified solution 2 is kept at 10° C. to 45° C., preferably 25° C. to 35° C. suited for alcoholic fermentation with yeast. The saccharified solution 2 is preferably stirred by a propeller 3 that is rotated by a motor M.

The saccharified solution 2 is preferably a saccharified solution (biomass saccharified solution) that is obtained by preparing a biomass material slurry by grinding cellulosic biomass (e.g. vegetation biomass such as bagasse, beet dregs, or straw) and mixing it with water, and treating the prepared biomass material slurry by a known method such as 1) method of hydrolyzing biomass by the oxidizing power of strong acid such as sulfuric acid, 2) method of hydrolyzing biomass enzymatically, or 3) method of hydrolyzing biomass by utilizing the oxidizing power of supercritical water or subcritical water. Not limited to the above, the saccharified solution 2 may be, for example, a solution containing saccharides obtainable by compressing biomass, molasses obtainable at the time of producing sugar, or a saccharified solution obtainable by saccharifying starch by acid or enzyme. When biomass is hydrolyzed by using strong acid, it is necessary to neutralize the strong acid before conducting alcoholic fermentation in the fermentation tank 1 so as not to inhibit the growth of yeast.

The saccharified solution 2 is drawn out from piping 4 connected below the fermentation tank 1. The piping 4 is provided with a pump P, and is connected with piping 5, and the fermented solution 2 is fed to a first membrane separator 7. The first membrane separator 7 is a membrane separator having a filtering membrane (microfiltering membrane) having a pore size of 0.5 µm or more and 5 µm or less, preferably a pore size of 0.5 µm or more and 1 µm or less. The flow rate of the fermented solution 2 fed in the order of fermentation tank 1→piping 4→piping 5→first membrane separator 7 is determined from the growth rate of the bacterial contaminants. Concretely, the flow rate is determined so that time Ts required for the fermented solution in the fermentation tank to take a round is smaller than doubling time Td of the bacterial contaminants in the fermented solution 2 (Td>Ts). Here, letting the volume of the fermentation tank 1 as V (L), and the flow rate of the fermented solution as v (L/min), Ts=V/v is satisfied.

Piping 6 is bypass piping for pressure adjustment for preventing the load of the pump P from being excessive, while it is piping for circulating fermented solution for drawing out the fermented solution in the bottom part so as to prevent yeast from settling when removal of bacterial contaminants is not conducted.

Yeast, which is about 5 to 10 µm in diameter, cannot pass through a filtering membrane having a pore size of 0.5 µm or more and 5 µm or less. On the other hand, bacteria having smaller diameters pass through the filtering membrane having a pore size of 0.5 µm or more and 5 µm or less. Therefore, by filtering the saccharified solution 2 by the first membrane separator 7, it is possible to recover the yeast in the saccharified solution in the state that it is contained in a concentrated saccharified solution (concentrated solution). The concentrated solution containing yeast is returned to the fermentation tank 1 from the upstream side (primary side) of the first membrane separator 7 via a path 8 and a path 9. A filtrate containing bacterial contaminants is fed to a second membrane separator 11 from the downstream side (secondary side) of the first membrane separator 7 via a path 10.

The second membrane separator 11 is a membrane separator having a filtering membrane (microfiltering membrane or ultrafiltering membrane) having a pore size of 0.22 µm or less. By filtering the saccharified solution 2 through the filtering membrane having a pore size of 0.22 µm or less, bacterial contaminants are removed from the saccharified solution 2, and the filtrate no longer contains bacterial contaminants. The filtrate from which bacterial contaminants have been removed (saccharified solution 2) is returned to the fermentation tank 1 from the downstream side (secondary side) of the second membrane separator 11 via a path 12 and the path 9. The concentrated solution containing bacterial contaminants is disposed of outside the system from the upstream side (primary side) of the second membrane separator 11 via a path 13.

As a result, in the fermentation system illustrated in FIG. 1, it is possible to continuously remove only bacterial contaminants from the saccharified solution 2 while recovering yeast in the saccharified solution 2 in the fermentation tank 1 repeatedly during execution of the alcoholic fermentation step in the fermentation tank 1. As the alcoholic fermentation progresses, saccharides contained in the saccharified solution 2 are converted to ethanol, and also as to the saccharified solution 2 (fermented solution) containing ethanol, only bacterial contaminants can be removed as is the case with a saccharified solution not containing ethanol before alcoholic fermentation.

After end of the alcoholic fermentation in the fermentation tank 1, the saccharified solution 2 (fermented solution) is drawn out from piping 14, and distilled by a distilling device, and is developed into a product as bioethanol.

Embodiment 2

Figure 2:
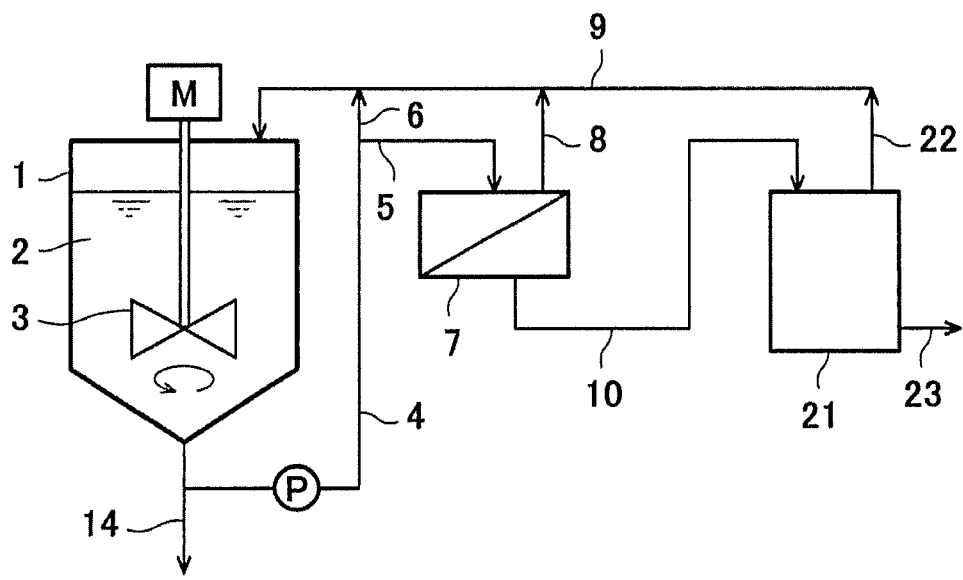
FIG. 2 is a schematic flowchart of a fermentation system according to Embodiment 2 of the present invention.

FIG. 2 is a schematic flowchart of a fermentation system according to Embodiment 2 of the present invention. The fermentation system illustrated in FIG. 2 has the same fundamental flow as the fermentation system of Embodiment 1 except that a centrifugal separator 21 is provided in place of the second membrane separator 11. Here, only a difference from that of the fermentation system of Embodiment 1 will be described.

The fermentation system of Embodiment 2 centrifugally separates the filtrate of the first membrane separator 7 at 1000G or higher and 15000G or lower by the centrifugal separator 21. Since bacterial contaminants contained in the saccharified solution 2 settle in the saccharified solution 2 under this centrifugal condition, it is possible to remove the bacterial contaminants from the saccharified solution 2 by taking out only the supernatant from the centrifugal separator 21. The supernatant from which bacterial contaminants have been removed is returned to the fermentation tank via piping 22 and the piping 9. On the other hand, the sediment containing bacterial contaminants is disposed of outside the system via piping 23.

Embodiment 3

Figure 3:
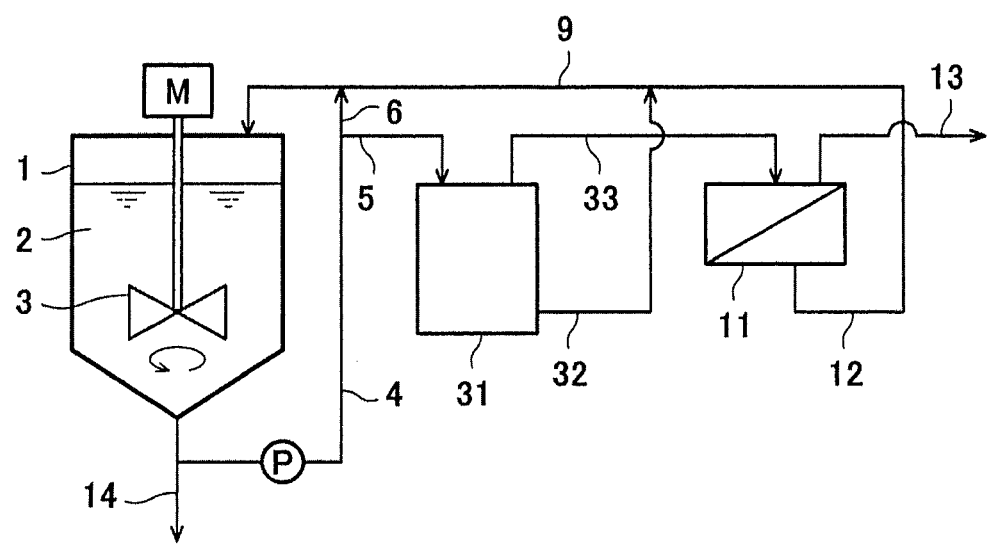
FIG. 3 is a schematic flowchart of a fermentation system according to Embodiment 3 of the present invention.

FIG. 3 is a schematic flowchart of a fermentation system according to Embodiment 3 of the present invention. The fermentation system illustrated in FIG. 3 has the same fundamental flow as the fermentation system of Embodiment 1 except that a centrifugal separator 31 is provided in place of the first membrane separator 7. Here, only a difference from that of the fermentation system of Embodiment 1 will be described.

The fermentation system of Embodiment 3 feeds part of the fermented solution 2 from the piping 5 to the centrifugal separator 31, and centrifugally separates it at 50G or higher and 500G or lower. Bacterial contaminants in the saccharified solution 2 do not settle but only yeast settles under this centrifugal condition. The sediment containing yeast is returned to the fermentation tank 1 via piping 32 and the piping 9. On the other hand, the supernatant of the saccharified solution 2 containing bacterial contaminants is fed to the membrane separator 11 from piping 33.

Embodiment 4

Figure 4:
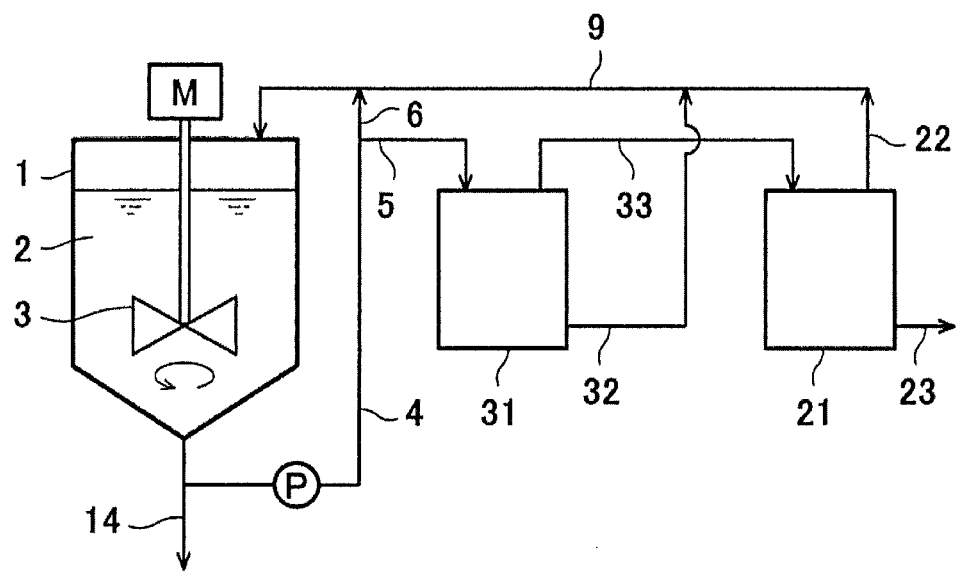
FIG. 4 is a schematic flowchart of a fermentation system according to Embodiment 4 of the present invention.

FIG. 4 is a schematic flow chart of a fermentation system according Embodiment 4 of the present invention. The fermentation system illustrated in FIG. 4 has the same fundamental flow as the fermentation system of Embodiment 3 except that the centrifugal separator 21 is provided in place of the second membrane separator 11. Here, only a difference from that of the fermentation system of Embodiment 3 will be described.

The fermentation system of Embodiment 4 feeds the supernatant of the saccharified solution taken out from the centrifugal separator 31 (first centrifugal separator) to the centrifugal separator 21 (second centrifugal separator) via piping 33, and centrifugally separates at 1000G or higher and 15000G or lower. Yeast is recovered by the centrifugal separator 31, and bacterial contaminants are removed from the saccharified solution by the centrifugal separator 21. Also by combining two centrifugal separators having different centrifugal separation conditions as described above, it is possible to recover only yeast from the saccharified solution and remove bacterial contaminants.

Example 1

Using the fermentation system of Embodiment 3, removal of bacterial contaminants from a saccharified solution in the fermentation tank was attempted. The saccharified solution is a saccharified solution that is obtained by treating rice straw with subcritical water, and has a saccharide concentration of 3.6% by mass (glucose 1.6% by mass+xylose 2.0% by mass). The saccharified solution was stored in a fermentation tank having an effective volume of 4.5 m$^3$ and kept at 26 to 30° C. *Pichia stipitis* (diameter about 4 μm) was added as yeast to the saccharified solution so that its concentration was $2\times10^8$ cells/mL, and stirred at a stirring speed of 60 rpm. At this time, the concentration of bacterial contaminants in the saccharified solution was $1\times10^6$ cells/mL or less. The mean particle size of bacterial contaminants was about 0.5 μm.

The concentration of bacterial contaminants in the saccharified solution increased with time and reached $5\times10^7$ cells/mL after a lapse of 12 hours. At this point of time, the pump P was started up, and the centrifugal separator (ADS3003CS available from SAITO SEPARATOR LIMITED) was supplied with the saccharified solution in a condition of 1.0 m$^3$/h, and centrifugation was conducted at 800G. Yeast that had been contained in the saccharified solution was rendered a yeast concentrated solution. A supernatant corresponding to 80% of the volume of the saccharified solution supplied to the centrifugal separator was fed to a membrane separator equipped with a microfiltering membrane having a pore size of 0.2 μm (Supor UEAV available from Pall Corporation). On the other hand, the remaining 20% that contains yeast was returned to the fermentation tank as a concentrated yeast solution. The filtrate of the membrane separator was returned to the fermentation tank, and the residue of filtration containing the bacterial contaminants was removed and disposed of by changing the microfiltering membrane every 24 hours.

The alcoholic fermentation was continued for 96 hours in the fermentation tank, and the concentration of bacterial contaminants in the saccharified solution (fermented solution) in the fermentation tank could be controlled to $1\times10^7$ cells/mL or less.

Example 2

Using the fermentation system of Embodiment 4, removal of bacterial contaminants from a saccharified solution in the fermentation tank was attempted. The saccharified solution was the same as that of Example 1, and the alcoholic fermentation condition of the fermentation tank and the upstream centrifugal separator for conducting rough separation are also identical to those of Example 1. The kind of yeast and the adding amount to the saccharified solution are also identical to those of Example 1.

After 12 hours from starting of the alcoholic fermentation, the concentration of bacterial contaminants in the saccharified solution reached $5\times10^7$ cells/mL. At this point of time, the pump P was started up, and the upstream first centrifugal separator for conducting rough separation was supplied with the saccharified solution at a condition of 1.1 m$^3$/h, and centrifugation was conducted at 500G for a retention time of 30 seconds. Yeast contained in the saccharified solution was returned to the fermentation tank similarly to Example 1.

The supernatant obtained by the first centrifugal separator was fed to the downstream second centrifugal separator (ADS3003CS available from SAITO SEPARATOR LIMITED) for conducting fine centrifugal separation, and centrifugally separated at 5000G. A supernatant corresponding to 99% of the supernatant of the saccharified solution fed to the second centrifugal separator was returned to the fermentation tank. The remaining saccharified solution was present as a paste solution containing bacterial contaminants, and was continuously taken out from the second centrifugal separator and disposed of.

Since the saccharified solution (fermented solution) in the fermentation tank gradually reduced, the saccharified solution was added appropriately to keep the liquid amount constant. The alcoholic fermentation was continued for 96 hours in the fermentation tank, and the concentration of bacterial contaminants in the saccharified solution (fermented solution) in the fermentation tank could be controlled to $1\times10^7$ cells/mL or less.

INDUSTRIAL APPLICABILITY

The method for removing bacterial contaminants from a saccharified solution and the fermentation system of the present invention are useful in energy fields such as bioethanol producing fields and brewing industry fields.

REFERENCE SIGNS LIST 1 fermentation tank
2 saccharified solution (fermented solution)
3 propeller (stirrer)
4,5,6,8,9,10,12,13,22,23,32,33 piping
7 membrane filtering device (first membrane filtering device)
11 membrane filtering device (second membrane filtering device)
21 centrifugal separator (second centrifugal separator)
31 centrifugal separator (first centrifugal separator)
M motor
P pump

The invention claimed is:
1. A method for producing ethanol, comprising:
a rough separation step A of recovering yeast without recovering bacterial contaminants by drawing out part of a saccharified solution in a fermentation tank, and centrifugally separating the saccharified solution by a first centrifugal separator at 50G or higher and 500G or lower;
a fine separation step B of separating bacterial contaminants from the saccharified solution from which yeast has been recovered, by centrifugally separating the saccharified solution by a second centrifugal separator at 1000G or higher and 15000G or lower after the rough separation step A;

a fermentation step C of fermenting the saccharified solution to alcohol with yeast in the fermentation tank to produce a fermentation solution; and a distillation step D of distilling the fermentation solution, after the step C, to produce ethanol, wherein by returning the yeast recovered by the rough separation step A, and the saccharified solution from which the bacterial contaminants have been separated by the fine separation step B to the fermentation tank, bacterial contaminants are selectively removed while the yeast in the saccharified solution is recovered.

* * * * *